United States Patent [19]

Buzas et al.

[11] Patent Number: 4,882,331
[45] Date of Patent: Nov. 21, 1989

[54] 1-[(1,1-DIPHENYL)-1-ALKENYL]PIPERAZINE DERIVATIVES, METHOD OF PREPARATION AND PHARMACEUTICAL COMPOSITIONS IN WHICH THEY ARE PRESENT

[75] Inventors: André Buzas, Bievres; Roland Ollivier, Olivet, both of France

[73] Assignee: Les Laboratoires Meram, France

[21] Appl. No.: 179,750

[22] Filed: Apr. 11, 1988

[30] Foreign Application Priority Data

Apr. 14, 1987 [FR] France .................................. 87 05311

[51] Int. Cl.⁴ ................. A61K 31/495; C07D 295/08; C07D 295/10
[52] U.S. Cl. ................................... 514/255; 544/396; 544/397
[58] Field of Search ................. 544/396, 397; 514/255

[56] References Cited

U.S. PATENT DOCUMENTS

| 2,882,271 | 4/1959 | Janssen | 544/396 |
| 3,267,104 | 8/1966 | Hermans et al. | 544/396 |
| 3,395,146 | 7/1968 | Satzinger | 544/396 |
| 3,773,939 | 11/1973 | Janssen | 544/396 |
| 4,113,972 | 9/1978 | Clark | 544/396 |
| 4,675,319 | 6/1987 | Nardi et al. | 544/396 |
| 4,703,048 | 10/1987 | Ohtaka | 544/396 |

FOREIGN PATENT DOCUMENTS

| 159566 | 10/1985 | European Pat. Off. | 544/396 |
| 207901 | 1/1987 | European Pat. Off. | 544/396 |
| 232205 | 8/1987 | European Pat. Off. | 544/396 |
| 256890 | 2/1988 | European Pat. Off. | 544/396 |
| 491579 | 1/1974 | Japan | 544/396 |
| 504086 | 1/1975 | Japan | 544/396 |
| 298579 | 12/1987 | Japan | 544/396 |

OTHER PUBLICATIONS

Hamlih et al, JACS, vol. 71, (1949), pp. 2734–2736.
Dorsett et al, Chem. Abst. 73-8758t, (1970).
Cirera et al., Chem. Abst. 107-17884s, (1987).
Buzas et al, CA 109-54672h, (1988).
Burzas et al, CA 109-149565q, (1988).
Journal of Medicinal Chemistry, vol. 15, No. 6, Jun. 1972, pp. 665–673, C. Kaiser et al., entitled "Analogs of Phenothiazines, 4. Effect of Structure upon Neuropharmacological Activity of Some Chlorpromazine Analogs of the Diphenylmethane Tupe".
Chemical Abstracts, vol. 107, No. 3, Jul. 20, 1987, Resume No. 17884s, X. D. Cirera et al., entitled "Preparation of Novel Compounds Derived from Diphenylmethyleneethylamine," and Span. Es-A-524,680 (Sociedad Espanola de Especialidades Farmaco-Terapeutics S.A.) Dec. 16, 1984.
Journal of Medicinal Chemistry, 1971, vol. 14, No. 2, "Substituted 1,1-Diphenyl-3-aminoprop-1-enes and 1,1-Diphenyl-3-aminopropanes as Potential Antidepressant Agents", pp. 161–164.

Primary Examiner—Cecilia Shen
Attorney, Agent, or Firm—Poms, Smith, Lande & Rose

[57] ABSTRACT

The invention relates to 1-[(1,1-diphenyl)-1-alkenyl]piperazine derivatives corresponding to general formula I:

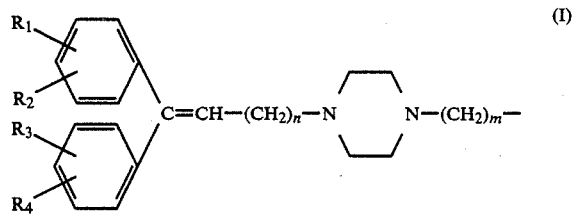

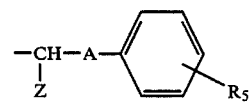

in which $R_1$, $R_2$, $R_3$, $R_4$ and $R_5$, which are identical or different, represent a hydrogen atom, a halogen atom, a lower alkyl group, a lower alkenyl group, a lower alkoxy group or the trifluoromethyl group; n is an integer between 1 and 3; m is an integer from 0 to 3; Z represents a hydrogen atom, a lower alkyl group or an aryl group of the formula:

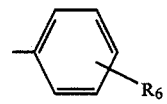

in which $R_6$ has the same meaning as $R_1$, $R_2$, $R_3$ or $R_4$; and A is an oxygen atom or a group

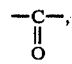

and to their pharmaceutically acceptable salts.

Application: pharmeutical compositions with antidepressant properties.

5 Claims, No Drawings

1-[(1,1-DIPHENYL)-1-ALKENYL]PIPERAZINE DERIVATIVES, METHOD OF PREPARATION AND PHARMACEUTICAL COMPOSITIONS IN WHICH THEY ARE PRESENT

The present invention relates to 1-[(1,1-diphenyl)-1-alkenyl]piperazine derivatives. It also relates to the pharmaceutically acceptable salts of these derivatives. A further subject of the present invention is the methods for their preparation and the pharmaceutical compositions in which they are present.

The derivatives according to the invention have valuable pharmacological properties on the central nervous system, in particular antidepressant properties, but possess little or no sedative activity.

The derivatives of the invention correspond to the following general formula:

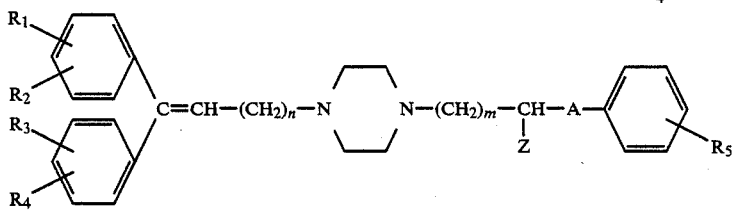

(I)

in which:

$R_1$, $R_2$, $R_3$, $R_4$ and $R_5$, which are identical or different, represent a hydrogen atom, a halogen atom, a lower alkyl group, a lower alkenyl group, a lower alkoxy group or the trifluoromethyl group;

n is an integer between 1 and 3;

m is an integer from 0 and 3;

Z represents a hydrogen atom, a lower alkyl group or an aryl group of the formula:

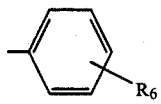

in which $R_6$ has the same meaning as $R_1$, $R_2$, $R_3$ or $R_4$; and

A is an oxygen atom or a group

In the present description:

"lower alkyl" denotes linear or branched, saturated aliphatic hydrocarbon radicals containing 1 to 6 carbon atoms; the preferred alkyl group for the purposes of the invention is the methyl group;

"lower alkenyl" denotes linear or branched, unsaturated aliphatic hydrocarbon radicals containing 1 to 6 carbon atoms; and "lower alkoxy" denotes a hydroxyl group substituted by a lower alkyl as defined above.

The compounds of the invention can be obtained by reacting a derivative of general formula II:

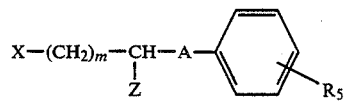

(II)

in which Z, m and A are as defined above and X is a tosyl group or a halogen atom (for example bromine or chlorine), with a substituted piperazine of general formula III:

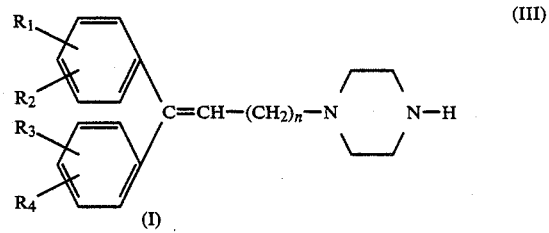

(III)

in which $R_1$, $R_2$, $R_3$, $R_4$ and n are as defined above, in the presence of sodium or potassium iodide and one equivalent of sodium or potassium carbonate.

This reaction is carried out by heating in an appropriate solvent such as an aromatic hydrocarbon, for example toluene or benzene, or in another solvent such as methyl ethyl ketone.

The derivatives of general formula III can easily be obtained by reacting a derivative of general formula IV:

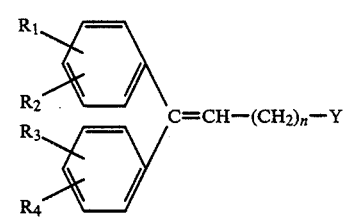

(IV)

in which $R_1$, $R_2$, $R_3$, $R_4$ and n are as defined above and Y is a bromine or chlorine atom, with anhydrous piperazine of formula V:

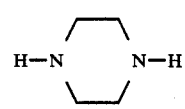

(IV)

In general, 4 equivalents of the compound of formula V are used per equivalents of the compound of formula IV.

This condensation reaction is carried out by refluxing in an appropriate solvent such as an aromatic hydrocarbon, for example benzene or toluene.

The compounds of formula IV can be prepared by the method described by DAVIS et al. in J. Med. Chem. 10, (4) 627–635, 1967.

The compounds of formula II in which m is an integer equal to 2, A is an oxygen atom, Z is an aryl radical, X is a chlorine atom and R₁, R₂, R₃, R₄ and R₅ are as defined above can also be obtained by the method described by SLIWA et al. in "Bull. Soc. Chim. Fra., 1972, 4, 1540–1544", according to the following reaction scheme:

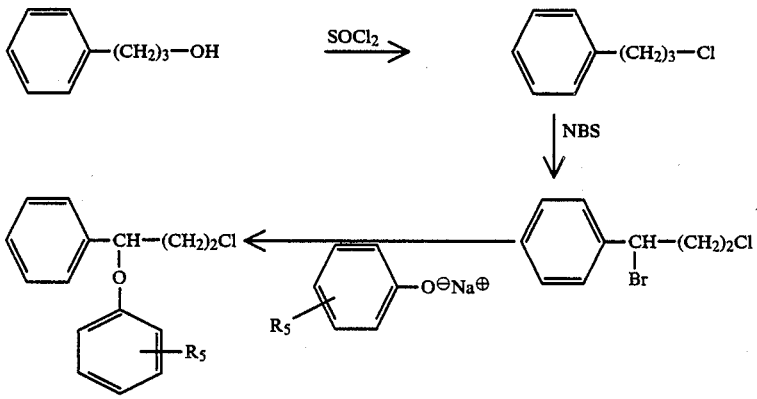

The other compounds of formula II in which A is oxygen can be obtained by conventional methods involving the addition of phenates onto dihalogenoalkyl compounds. Some of these compounds are available commercially.

The compounds of formula II in which A is the group

can be obtained by the well-known Friedel-Crafts reaction. In the examples which follow, commercially available parafluorobutyrophenone chloride was used.

The acid addition salts of the derivatives of formula I according to the invention can be obtained by conventional methods with acids commonly used for the preparation of pharmaceutically acceptable salts, such as hydrochloric acid, methanesulfonic acid, tartaric acid, maleic acid or fumaric acid.

As stated above, the derivatives according to the invention possess valuable pharmacological properties on the central nervous system and especially antidepressant properties.

Therefore the invention also relates to the pharmaceutical compositions in which a derivative according to the invention is present as the active principle, in combination with a pharmaceutically acceptable vehicle.

The compositions according to the invention can be administered orally or by injection. They can take the form of solutions, tablets, gelatin capsules, pills or injectable compositions.

The invention will now be described in greater detail by means of the illustrative examples which follow. In these examples, the derivatives prepared were identified and characterized by studying their NMR and infrared spectra and also by their elemental analyses.

The piperazine derivative used as the starting compound was prepared by the following procedure: Preparation of 1-[(1,1-diphenyl)-1-buten-4-yl]piperazine A solution of 34.4 g of anhydrous piperazine in 110 ml of toluene was placed in a 250 ml reactor. The mixture was heated to the reflux temperature and a solution of 28.7 g of 4-bromo-1,1-diphenyl-1-butene in 15 ml of toluene was added dropwise. The mixture was stirred for 1 h.

The solution was cooled. After filtration, it was taken up with 100 ml of water and decanted. The toluene phase was extracted with 3 times 50 ml of a 7% solution of acetic acid. The extract was neutralized with sodium carbonate in the presence of 100 ml of $CH_2Cl_2$. The organic phase was decanted and dried and the solvent was evaporated off. 22.5 g of a brown oil were collected; this was used in the crude state in the next example. Empirical formula: $C_{20}H_{24}N_2O$.

NMR spectrum (solvent $CDCl_3$, reference TMS):
1.2 ppm (s), 1H, NH; 2.2 ppm (m), 8H, $CH_2$—N—$CH_2$—$CH_2$—C=C; 2.7 ppm (m), 4H, H-N-$CH_2$; 5.8 ppm (t), 1H, C=CH; 7.0 ppm (M), 10H, φ.

EXAMPLE 1 Preparation of 1-[(1,1-diphenyl)-1-buten-4-yl]-4-[1-(2-(4-fluorophenoxy)ethyl]piperazine dimethanesulfonate (1)

A solution of 13.33 g of 1-(1,1-diphenyl-1-buten-4-yl)piperazine, obtained in Example 1, in 150 ml of methyl ethyl ketone, 10 g of 2-bromo-1-(4-fluorophenoxy)ethane, 9.45 g of $Na_2CO_3$ and 0.1 g of anhydrous NaI were placed in a 250 ml reactor.

The reaction mixture was refluxed for 18 h and then cooled. After filtration, the solution was washed twice with 80 ml of water.

It was decanted and dried and the solvent was evaporated off. 10.5 g of a yellow oil were collected.

To purify the product, the hydrochloride was prepared and recrystallized from acetone.

100 ml of a 1N solution of hydrochloric acid were added to 7 g of the crude oil obtained above. The mixture was stirred for 30 min. After filtration and rinsing twice with 50 ml of water, the hydrochloride obtained was crystallized from 30 ml of acetone.

The base was freed with $Na_2CO_3$ in the presence of 50 ml of water and 50 ml of $CH_2Cl_2$. The organic phase was decanted and dried and the solvent was evaporated off to give 6.3 g of an oil.

The dimethanesulfonate was prepared by reacting a solution of 4 g of the resulting product in ether with 1.8 g of methanesulfonic acid to give a solid with a melting point of 150° C. and the empirical formula: $C_{28}H_{31}FN_2O.2(CH_4O_3S)$.

NMR spectrum of the base (solvent $CDCl_3$, reference TMS):

2.5 ppm (M), 14H, =C—C$\underline{H_2}$—C$\underline{H_2}$—N—C$\underline{H}$$_2$—C$\underline{H_2}$; 4.0 ppm (t), 2H, O—CH$_2$; 6.0 ppm (t), 1H, C=CH; 7.0 ppm (m), 14H, φ.

IR spectrum (1% in KBr):

2500 cm$^{-1}$ (N$^+$—H); 1200 cm$^{-1}$ (SO$_2$); 1060 cm$^{-1}$ (SO$_2$).

EXAMPLES 2 to 17

Compounds no. 2 to 17 indicated in the table below were obtained by following the procedure described in Example 1 above.

Derivative 6: 2.0 ppm (m), 2H, C—CH$_2$—C—O; 2.3 ppm (m), 14H, CH$_2$—CH$_2$—N; 3.7 ppm (t), 2H, O—CH$_2$; 5.8 ppm (t), 1H, C=CH; 6.5 to 7.2 ppm (m), 14H, φ.

Derivative 7: 1.6 to 2.6 ppm (m), 16H, CH$_2$—CH$_2$—N; 1.8 ppm (t), 2H, CH$_2$—C=O; 5.8 ppm (t), 2H, C=CH; 6.5 to 7.8 ppm (m), 14H, φ.

Derivative 8: 1.8 ppm (m), 4H, N—C—CH$_2$—CH$_2$—C—O; 2.3 ppm (m), 12H, CH$_2$—N; 3.7 ppm (t), 2H, O—CH$_2$; 5.8 ppm (t), 1H, C=CH; 6.5 to 7.4 ppm (m), 14H, φ.

Derivative 9: 2.4 ppm (m), 14H, CH$_2$—CH$_2$—N—CH$_2$—CH$_2$—N—CH$_2$; 4.0 ppm (t), 2H, CH$_2$O; 6.0 ppm (t), 1H, C=CH; 7.2 ppm (m), 15H, φ.

Derivative 10: 1.2 ppm (s), 9H, CH$_3$; 1.9 ppm (m), 2H, C—CH$_2$—C; 2.3 ppm (m), 14H, CH$_2$—N; 4.0 ppm (t), 2H; CH$_2$O; 6.0 ppm (t), 1H, C=CH; 1.0 ppm (m),

TABLE I

General structure: $R_1, R_2, R_3, R_4$-substituted diphenyl C=CH—(CH$_2$)$_n$—N(piperazine)N—(CH$_2$)$_m$—CH(Z)—A—phenyl-$R_5$

| Compound | $R_1 = R_2 = R_3 = R_4$ | $R_5$ | Z | n | m | A | Melting point °C. | Molecular weight | Salt |
|---|---|---|---|---|---|---|---|---|---|
| 1 | H | 4-F | H | 2 | 1 | O | 150 | 622 | Dimethanesulfonate |
| 2 | H | 2-CH$_3$ | H | 2 | 1 | O | 100$^a$ | 618 | |
| 3 | H | 3-Cl | H | 2 | 1 | O | 90$^a$ | 638.5 | |
| 4 | H | 2-CH$_3$ | phenyl | 2 | 2 | O | 80$^a$ | 708 | |
| 5 | H | 4-F | " | 2 | 2 | O | 85$^a$ | 712 | |
| 6 | H | 4-F | H | 2 | 2 | O | 155 | 636 | |
| 7 | H | 4-F | H | 2 | 2 | C=O | 140 | 648 | |
| 8 | H | 4-F | H | 2 | 3 | O | 134 | 650 | |
| 9 | H | H | H | 2 | 1 | O | 200 | 604 | |
| 10 | H | 4-t(C$_4$H$_9$) | H | 2 | 2 | O | 222 | 674 | |
| 11 | H | 4-Cl | H | 2 | 2 | O | 156 | 625.5 | |
| 12 | H | 3-OCH$_3$ | H | 2 | 2 | O | 189 | 648 | |
| 13 | H | 4-F | H | 2 | 3 | O | 154 | 650 | |
| 14 | H | 4-CH$_3$ | H | 2 | 3 | O | 157 | 646 | |
| 15 | H | 4-t(C$_4$H$_9$) | H | 2 | 3 | O | 191 | 688 | |
| 16 | H | 4-F | H | 3 | 1 | O | 165 | 636 | |
| 17 | $R_1 = 4$-F, $R_2 = R_3 = R_4 = H$ | 4-F | H | 2 | 1 | O | 151 | 640 | |

$^a$decomposition point

The NMR spectra of these compounds are given below (solvent $CDCl_3$—internal reference TMS):

Derivative 2: 2.3 ppm (s), 3H, CH$_3$; 2.5 ppm (m), 14H, C$\underline{H_2}$—C$\underline{H_2}$—N—C$\underline{H_2}$—C$\underline{H_2}$—N; 4.1 ppm (t), 2H, O—C$\underline{H_2}$; 6.1 ppm (t), 1H, C=CH; 7.0 ppm (m), 14H, φ.

Derivative 3: 2.5 ppm (m), 14H, C$\underline{H_2}$—C$\underline{H_2}$—N—C$\underline{H}$$_2$—C$\underline{H_2}$—N: 4.0 ppm (t), 2H, O—C$\underline{H_2}$; 6.0 ppm (t), 1H, C=CH; 7.0 ppm (m), 14H, φ.

Derivative 4: 2.3 ppm (m), 16H, C$\underline{H_2}$—C$\underline{H_2}$—N—C$\underline{H}$$_2$—C$\underline{H_2}$—N—C$\underline{H_2}$; 2.4 ppm (s), 3H, CH$_3$; 5.1 ppm (t), 1H, C$\underline{H}$—O; 5.9 ppm (t), 1H, C=CH; 7.1 ppm (m), 19H, φ.

Derivative 5: 2.4 ppm (m), 16H, C$\underline{H_2}$—C$\underline{H_2}$—N—C$\underline{H}$$_2$—C$\underline{H_2}$—N—C$\underline{H_2}$; 5.1 ppm (t), 1H, O—C$\underline{H}$; 6.0 ppm (t), 1H, C=C$\underline{H}$; 7.0 ppm (m), 19H, φ.

14H, φ.

Derivative 11: 1.8 ppm (m), 2H, CH$_2$; 2.4 ppm (m), 14H, CH$_2$N; 3.9 ppm (t), 2H, CH$_2$O; 6.0 ppm (t), 1H, C=CH; 7.0 ppm (m), 14H, φ.

Derivative 12: 2.3 ppm (m), 16H, CH$_2$—N, CH$_2$; 3.5 ppm (s), 3H, CH$_3$O; 3.7 ppm (t), 2H, CH$_2$O; 5.9 ppm (t), 1H, C=CH; 6.7 to 7.4 ppm (m), 14H, φ.

Derivative 13: 1.7 to 2.4 ppm (m), 18H, CH$_2$—N, CH$_2$; 3.8 ppm (t), CH$_2$O; 6.0 ppm (t), 1H, C=CH; 6.8 to 7.2 ppm (m), 14H, φ.

Derivative 14: 1.8 ppm (m), 4H, N—C—CH$_2$—CH$_2$—C—O; 2.4 ppm (s), 3H, CH$_3$; 2.3 to 2.6 ppm (m), 14H, CH$_2$—CH$_2$—N—CH$_2$—CH$_2$—N—CH$_2$; 3.9 ppm (t), 2H, CH$_2$—O; 6.0 ppm (t), 1H, CH=C; 6.5 to 7.2 ppm (m), 14H, φ.

Derivative 15: 1.2 ppm (s), 9H, CH$_3$; 1.7 ppm (m), 4H, N—C—CH$_2$—CH$_2$—C—O; 2.1 to 2.6 ppm (m), 14H, CH$_2$—CH$_2$—N—CH$_2$—CH$_2$—N—CH; 3.8 ppm (t), 2H, CH$_2$—O; 6.0 ppm (t), 1H, CH=C; 6.3 to 7.3 ppm (m), 14H, $\phi$.

Derivative 16: 1.6 to 3.3 ppm (m), 16H, CH$_2$—CH$_2$—CH$_2$—N—CH$_2$—CH$_2$—N—CH$_2$—C—O; 4.0 ppm (t), 2H, CH$_2$—O; 6.0 ppm (t), 1H, CH=C; 6.7 to 7.4 ppm (m), 14H, $\phi$.

Derivative 17: 2.2 to 2.7 ppm (m), 4H, CH$_2$—N, CH$_2$—C=C; 4.0 ppm (t), 2H, CH$_2$—O; 6.0 ppm (t), 1H, CH=C; 6.8 to 7.4 ppm (m), 13H, $\phi$.

I - TOXICITY TEST

The toxicity of the compounds of the invention was determined by the following test:

Determination of the 50% lethal dose (LD$_{50}$) in mice

The test product was administered intraperitoneally to groups of 5 male mice and 5 female mice at a rate of 0.1 ml per 10 g of body weight.

The following doses were used:
100—150—200—300—400 mg.kg$^{-1}$ IP

The LD$_{50}$ determined from the mortality observed is indicated in the following table, together with that of the known antidepressants AMINEPTINE and IMIPRAMINE.

TABLE II

| No. | LD$_{50}$ IP mg/kg | FIDUCIAL LIMITS CALCULATION ACCORDING TO LITCHFIELD and WILCOXON |
|---|---|---|
| 1 | 231 | 195–274 |
| 2 | #200 | — |
| 3 | #250 | — |
| 4 | 386 | 279–453 |
| 5 | 314 | 234–421 |
| 6 | 247 | 206–296 |
| 7 | #175 | — |
| 8 | 199 | 172–229 |
| AMINEPTINE | #200 | — |
| IMIPRAMINE | #115 | — |

II - PHARMACOLOGICAL TESTS

The pharmacological properties of the compounds of the invention were determined using the following tests:

Experimental protocols

1. Study of the spontaneous motility

The motor activity of mice was determined using a Boissier and Simon photoelectric actimeter.

The mice are placed in groups of five in a box closed with a lid, through which two perpendicular rays of light pass; the mice cut across these rays as they move.

These movements are counted by a meter, which is read 30 min and 1 h after the administration of the test derivative.

2. Exploratory behavior 30 min after the intraperitoneal administration of the derivatives according to the invention, each mouse is placed on an automated hole-board for 5 min and the number of holes explored is noted every minute.

A 50% effective dose can be calculated from the results obtained.

3. Muscle-relaxing action (traction test)

This test assesses the presence or absence of redressments in a mouse brought up to a horizontal wire with its front paws.

The number of mice which are unable to grip the wire with one of their back paws within 5 s is noted.

A 50% effective dose can be calculated from the results obtained.

4. Rectal temperature

The rectal temperature of mice is measured using an Ellab. ctd 85 electric thermometer.

A first reading is taken immediately before the injection of the test derivative.

The temperature is noted 30 min and 1, 2, 3 and 4 h after the injection.

5. Peripheral analgesic activity

A peritoneal pain is caused in mice by the intraperitoneal injection of phenylbenzoquinone (PBQ).

The test assesses the decrease in the pain syndrome, characterized by an abdominal twisting movement, which is caused by injecting the test derivative 30 min before the administration of PBQ.

The 50% effective dose is calculated from the percentage decrease in the pain syndrome relative to the control animals.

6. Central analgesic activity

This test assesses an increase in the time which is spent on a plate, heated to 60° C., by mice treated with the test derivative 30 min before the start of the test.

The 50% effective dose is calculated from the percentage increase in the time spent on the hotplate (licking of the paws or, in some cases, jumping).

7. Interaction with pentobarbital

This test assesses any increase in the sleep induced by barbiturate which is caused by administering the test derivative intraperitoneally 5 min before the intraperitoneal injection of pentobarbital (37.5 mg/kg).

A 50% effective dose can be calculated from the results obtained.

8. Interaction with oxotremorine

As oxotremorine is an agonist of cholinergic receptors, substances which antagonize the trembling, hypothermia and peripheral signs (salivation, piloerection) induced by this product can be considered to be anticholinergics.

The test derivative is administered 30 min before the intraperitoneal injection of oxotremorine.

9. Yohimbine test

The test derivative is administered 30 min before the injection of yohimbine (25 mg/kg IP).

The number of deaths is counted 24 h after the injection of yohimbine.

10. Apomorphine test

The test derivative is administered intraperitoneally 30 min before the injection of apomorphine. Apomorphine is injected subcutaneously at a rate of 16 mg/kg.

The mice are then isolated in small cages.

The redressments, stereotypies and rectal temperature of the animals are noted.

11. Reserpine test

The test derivative is administered intraperitoneally. The mice are placed in individual cages.

Reserpine (2.5 mg/kg) is injected intraperitoneally 30 min after the injection of the test derivative.

The occlusion of the eyelids is noted every 30 min and the rectal temperature is taken 2 h, 3 h and 4 h after the injection of reserpine.

12. Anticataleptic test with prochloroperazine (PCPZ)

The test derivative is injected and each rat is placed in an individual cage.

25 mg/kg of PCPZ are injected 30 min later.

Every 30 min, each rat is placed on a sheet of filter paper and its front paws are crossed with the back paws on the same side.

13. Porsolt's test

The test derivative is administered intraperitoneally 60 min before the start of the test.

The mice are then placed in a beaker half-filled with water for 6 min.

The time which the animals spend moving in the water is calculated.

14. Tail suspension test (TST)

A rodent placed in a disagreeable situation with no obvious means of escape (hanging by its tail) rapidly tends to reduce its evasive motor activity.

The apparatus comprises two suspending units, a central unit and a microcomputer which integrates the operator's commands and the statistical calculations.

The test derivative is administered intraperitoneally 30 min before the mice are suspended.

The various parameters (immobility time, total energy, power of the movements) are measured automatically for 6 min.

Results

The results obtained are collated in Table III below. These results show that the derivatives of the invention are active on the central nervous system and have antidepressant properties in particular.

Comparative tests

By way of comparison, the above tests were carried out with AMINEPTINE, IMIPRAMINE and MIANSERINE, which are products known for their antidepressant properties. The results obtained are also included in Table III below. These results show that the derivatives of the invention, and especially compound no. 1, are antidepressants with a greater activity than the known antidepressants.

The compound of Example 1 was furthermore tested for its antiserotoninergic activity according to the following tests:

Experimental protocols

1. Head twitches caused by 5-hydroxytryptophane (5-HTP)

Animals: male mice of $25\pm1$ g

At time T-3 h, 100 mg/kg of pargyline were injected intraperitoneally.

At time T-30 minutes, the test product or distilled water (control) was injected intraperitoneally.

At time T=O, 5-HTP was injected intraperitoneally at a dose of 4 mg/kg.

All the jerky head movements made by the mice were observed over a 1-minute period every twelve minutes.

The mean number of movements was calculated and compared with the control group.

2. Head twitches caused by 5-methoxydimethyltryptamine (5-MeODMT)

Animals: male mice of $25\pm1$ g

At time T-3 hours, 100 mg/kg of pargyline were injected intraperitoneally.

At time T-30 minutes, the test product or distilled water (control) was injected intraperitoneally.

At time T=O, 5-MeODMT was injected intraperitoneally at a dose of 4 mg/kg.

The number of head twitches was observed.

The mean number of movements was calculated and compared with the control group.

3. Penile erections caused by apomorphine

The test product was administered parenterally or orally to rats, placed in a transparent cage, 30 minutes before the intraperitoneal injection of 0.20 mg/kg of apomorphine.

The number of penile erections was recorded over the 30 minutes following the injection of apomorphine.

A statistical study was carried out by comparison with the numbers of erections in the control rats.

4. Tryptamine test

Tryptamine causes characteristic convulsive seizures in rats.

The test product was administered intraperitoneally 1 hour before the intravenous injection of tryptamine (40 mg/kg).

The ability of the product to reduce the intensity and/or duration of the convulsive seizure was observed.

Statistical calculations were made by comparison with the results observed in the control animals.

5. Grahame Smith's test

Animals: male rats of $200\pm10$ g

At time T-30 minutes, the test product was administered intraperitoneally.

At time T=O, an MAOI was administered intraperitoneally (tranylcypromine, 20 mg/kg).

At time T+20 minutes, 250 mg/kg of tryptophan were administered (IP).

The temperature of the rats was recorded every 30 minutes for 200 minutes and the various clinical signs (motor agitation—hypersalivation—catatonia of the tail—hyperesthesia—thrashing of the tail, etc.) were noted on a scale of 0 to 1.

The mean temperatures and the average symptoms observed were calculated by comparison with the controls.

Results

The results obtained are collated in Table IV below. These results show that the compound of Example 1 possesses an antiserotoninergic activity.

TABLE III

| | Activity mouse mg·kg⁻¹ IP | Exploratory behavior mouse mg·kg⁻¹ IP | Muscle-relaxing action Traction test mouse mg·kg⁻¹ IP | Rectal temperature mouse | Peripheral analgesic activity mouse ED50 mg·kg⁻¹ IP | Central analgesic activity mouse mg·kg⁻¹ IP | Narcosis induced by barbiturate mouse | Interaction with oxotremorine mouse | Yohimbine toxicity mouse ED50 mg·kg⁻¹ IP | Antagonism of the symptoms induced by APOMORPHINE 16 mg·kg⁻¹ SC mouse mg·kg⁻¹ IP | Antagonism of the symptoms induced by RESERPINE mouse mg·kg⁻¹ IP | Interaction with PCPZ rat mg·kg⁻¹ IP | Porsolt's test mouse mg·kg⁻¹ IP | TST mouse mg·kg⁻¹ IP |
|---|---|---|---|---|---|---|---|---|---|---|---|---|---|---|
| 1 | No modification up to 25 | No modification up to 25 | No modification up to 25 | Transient hypothermia | 1.50 | No activity up to 12.5 | No increase in the sleep induced by barbiturate | No antagonism | 31 | Antagonizes the hypothermia at 6.25 | Antagonizes the hypothermia at 3.12 | Antagonizes the catalepsy at 25 | Active up to 3.12 | Active up to 3.12 |
| 2 | — | No modification up to 25 | — | No modification | — | No activity | — | No antagonism | Increase above 6.25 | No antagonism | Practically zero antagonism | — | Active at 25 | Active at 25 |
| 3 | — | No modification up to 25 | — | No modification | — | No activity | Increase in the sleep induced by barbiturate | No antagonism | Substantial increase at 12.5 | No antagonism | Very slight antagonism | — | Active at 12.5 | Active at 25 |
| 4 | Increase | No modification up to 25 | — | No modification | 1.50 | No activity | No increase | No antagonism | Slight increase | No antagonism | Antagonizes the hypothermia at 12.5 | Antagonizes the catalepsy at 12.5 and 25 | Inactive | Inactive |
| 5 | No modification up to 25 | No modification up to 25 | No modification up to 25 | No modification | — | No activity | Increase in the sleep induced by barbiturate at 25 mg·kg⁻¹ | No antagonism | No increase | No antagonism | Antagonizes the hypothermia at 12.5 | — | Inactive | Inactive |
| 6 | Distinct decrease | No modification up to 25 | No modification up to 25 | — | Slight activity | No activity up to 25 | Slight increase in the sleep induced by barbiturate | No antagonism | 25 | No antagonism | Antagonizes the hypothermia at 12.5 | No antagonism at 25 | Inactive | Inactive |
| 7 | ED50 7.5 mg·kg⁻¹ | No modification up to 25 | No modification up to 25 | Hypothermia at 25 | 0 | — | Increase in the sleep induced by | No antagonism | >25 | No antagonism | No antagonism | No antagonism | Inactive | — |

TABLE III-continued

| PRODUCT | Activity mouse mg·kg⁻¹ IP | Exploratory behavior mouse mg·kg⁻¹ IP | Muscle relaxing action Traction test mouse mg·kg⁻¹ IP | Rectal temperature mouse | | | barbiturate | | | | |
|---|---|---|---|---|---|---|---|---|---|---|---|
| 8 | Decrease at 25 | No modification up to 25 | No modification up to 25 | Transient hypothermia | 6.25 | Slight increase in the sleep induced by barbiturate | No antagonism | >25 | No antagonism | Antagonizes the hypothermia at 12.5 | Inactive | — |
| 14 | Decrease | No modification | No modification | No modification | 2.5 | Increase in the sleep induced by barbiturate at 4.9 | Antagonizes the hypothermia | >25 | Antagonizes the hypothermia | Antagonizes the hypothermia | Active at 25.0 | Active at 25.0 |
| 16 | Substantial increase | No modification | No modification | No modification | 4.5 | No increase | Antagonizes the hypothermia | Little activity | No antagonism | Practically inactive | Inactive | Increase in the energy and power of the movements |
| 17 | Increase at 7.9 | No modification | Active at 25 | No modification | 5.2 | No increase | No antagonism | >25 | Antagonizes the hypothermia at 6.25 | Slight antagonism | Active at 6.25 | Very active at 1.58 |

| PRODUCT | Peripheral analgesic activity mouse ED₅₀ mg·kg⁻¹ IP | Central analgesic activity mouse mg·kg⁻¹ IP | Interaction with oxotremorine mouse | Yohimbine toxicity mouse ED₅₀ mg·kg⁻¹ IP | Antagonism of the symptoms induced by APOMORPHINE 16 mg·kg⁻¹ SC mouse mg·kg⁻¹ IP | Antagonism of the symptoms induced by RESERPINE mouse mg·kg⁻¹ IP | Interaction with PCPZ rat mg·kg⁻¹ IP | Porsolt's test mouse mg·kg⁻¹ IP | TST mouse mg·kg⁻¹ IP |
|---|---|---|---|---|---|---|---|---|---|
| AMINEPTINE | — | — | No antagonism | Increase above 10 | No antagonism | Antagonizes the hypothermia | — | Active at 6.25 | Active at 12.5 |
| IMIPRAMINE | — | — | Decreases the trembling | Increase above 15 | Antagonizes the hypothermia | Antagonizes the hypothermia | Antagonizes at 15 | Active at 8 | Active at 8 |
| MIANSERINE | — | — | — | — | — | — | — | Active at 16 | Active at 3.13 |

TABLE IV

| | ANTISEROTONINERGIC ACTIVITY | | | | |
|---|---|---|---|---|---|
| | Antagonism of the head twitches induced by | | Antagonism of the penile erections and yawning (rats) | Tryptamine test (rats) | Grahame Smith's test (rats) |
| | 5-HTP | 5-MeODMT | | | |
| Compound 1 (IP) | ↓ as from 18.8 mg/kg | ↓ as from 6.25 mg/kg | antagonism as from 6.25 mg/kg | active as from 50 mg/kg | ↓ hyperthermia and clinical signs |
| Compound 1 (PO) | nt | nt | nt | nt | ↓ at 37.5 mg/kg |
| Mianserin (IP) | nt | nt | nt | active at 6.0 mg/kg | | nt = not tested

We claim:

1. 1-[(1,1-Diphenyl)-1-alkenyl]piperazine derivatives corresponding to formula I:

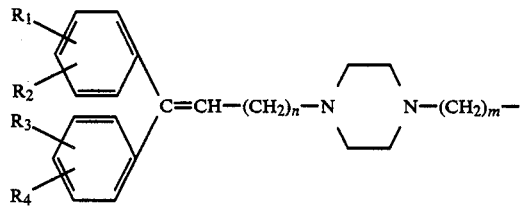

in which:
R$_1$, R$_2$, R$_3$, R$_4$ and R$_5$, which are identical or different, represent a hydrogen atom, a halogen atom, a lower alkyl group, a lower alkenyl group, a lower alkoxy group or the trifluoromethyl group;
n is an integer from 1 to 3;
m is an integer from 0 to 3;
Z represents a hydrogen atom, a lower alkyl group or an aryl group of the formula:

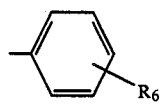

in which
R$_6$ has the same meaning as R$_1$, R$_2$, R$_3$ or R$_4$; and
A is an oxygen atom or a group

and their pharmaceutically acceptable salts.

2. Derivative according to claim 1, which is 1-[(1,1-diphenyl)-1-buten-4-yl]-4-[1-(2-(4-fluorophenoxy)ethyl]-piperazine.

3. A method for the preparation of the derivatives as claimed in claim 1, which consists in reacting a derivative of general formula II:

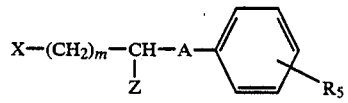

in which Z, m and A are as defined above and X is a tosyl group or a halogen atom (for example bromine or chlorine), with a piperazine of general formula III:

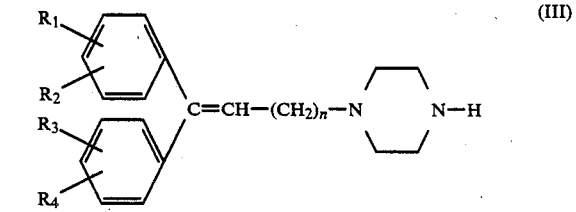

in which R$_1$, R$_2$, R$_3$, R$_4$ and n are as defined above; in the presence of sodium or potassium iodide and one equivalent of sodium or potassium carbonate, and in converting the resulting compounds to their pharmaceutically acceptable salts.

4. A pharmaceutical composition for use in treating depressant in which an antidepressant effective amount of a derivative as claimed in claim 1 is present as the active ingredient, in combination with a pharmaceutically acceptable vehicle.

5. A method for treating depressant which comprises administrating an antidepressant effective amount of a piperazine derivative corresponding to formula I:

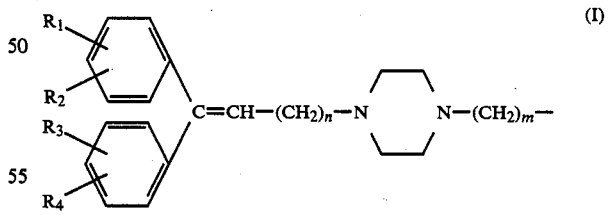

in which:
R$_1$, R$_2$, R$_3$, R$_4$ and R$_5$, which are identical or different represent a hydrogen atom, a halogen atom, a lower alkyl group, a lower alkenyl group, a lower alkoxy group or the trifluoromethyl group;
n is an integer from 1 to 3;

m is an integer from 0 to 3;
Z represents a hydrogen atom, a lower alkyl group or an aryl group of the formula:
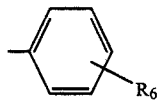
in which
$R_6$ has the same meaning as $R_1$, $R_2$, $R_3$ or $R_4$; and
A is an oxygen atom or a group
and their pharmaceutically acceptable salts for the manufacture of drugs active on the central nervous system.
* * * * *